United States Patent [19]

Shimomura et al.

[11] Patent Number: 5,200,053

[45] Date of Patent: Apr. 6, 1993

[54] REFERENCE ELECTRODE

[75] Inventors: Takeshi Shimomura; Shuichiro Yamaguchi; Naoto Uchida; Takehisa Mori, all of Kanagawa; Teruaki Katsube, Tama, all of Japan

[73] Assignee: Terumo Kabushiki Kaisha, Tokyo, Japan

[21] Appl. No.: 490,636

[22] PCT Filed: Nov. 24, 1988

[86] PCT No.: PCT/JP88/01188

§ 371 Date: May 24, 1990

§ 102(e) Date: May 24, 1990

[87] PCT Pub. No.: WO89/04959

PCT Pub. Date: Jan. 6, 1989

[30] Foreign Application Priority Data

Nov. 24, 1987 [JP] Japan .................. 62-293957
Oct. 27, 1988 [JP] Japan .................. 63-271784

[51] Int. Cl.⁵ ........................... G01N 27/26
[52] U.S. Cl. ...................... 204/435; 204/416; 204/419
[58] Field of Search .............. 204/435, 432, 419, 416

[56] References Cited

U.S. PATENT DOCUMENTS

| | | | |
|---|---|---|---|
| 3,591,482 | 7/1971 | Neff et al. | 204/419 |
| 4,002,547 | 1/1977 | Neti et al. | 204/435 |
| 4,053,382 | 10/1977 | Maruyama et al. | 204/435 |
| 4,211,623 | 7/1980 | Ross, Jr. et al. | 204/419 |
| 4,214,968 | 7/1980 | Battaglia et al. | 204/418 |
| 4,259,164 | 3/1981 | Rasch et al. | 204/419 |
| 4,263,343 | 4/1981 | Kim | 204/435 |
| 4,269,682 | 5/1981 | Yano et al. | 204/435 |
| 4,507,194 | 3/1985 | Shimomura et al. | 204/435 |
| 4,512,870 | 4/1985 | Kohara et al. | 204/416 |
| 4,636,294 | 1/1987 | Novack et al. | 204/432 |
| 4,645,583 | 2/1987 | Shirai et al. | 204/435 |
| 4,933,048 | 6/1990 | Lauks | 204/435 |

FOREIGN PATENT DOCUMENTS

| | | |
|---|---|---|
| 186286 | 10/1985 | European Pat. Off. |
| 366566 | 10/1989 | European Pat. Off. |
| 208706 | 7/1982 | Fed. Rep. of Germany |
| 54-81897 | 6/1979 | Japan |
| 59-24242 | 7/1984 | Japan |
| 59-214751 | 12/1984 | Japan |
| 2190399 | 5/1986 | United Kingdom |

OTHER PUBLICATIONS

International Search Report (PCT/JP 88/01188).
Supplementary European Search Report (EP 88 91 0119).
Patent Abstracts of Japan, vol. 11, No. 276 relating to "Japanese Patent Document No. 62-75250").

Primary Examiner—John Niebling
Assistant Examiner—Bruce Bell
Attorney, Agent, or Firm—Burns, Doane, Swecker & Mathis

[57] ABSTRACT

A reference electrode according to the present invention includes a silver layer (2) and an insulating hydrophobic material layer (5) which is formed by atomic beam sputtering and containing silver halide dispersed therein, on the surface of a conductive substrate (1).

The resulting reference electrode is of a solid type, is almost free from outflow of silver halide, can be miniaturized easily, is not affected by ion concentration, provides a stable potential and has high durability.

The conductive substrate (1) may be a field effect transistor having a gate insulator film and the layer (5) may be a laminate film obtained by laminating alternately a thin layer or layers of silver halide and a thin layer or layers of insulating hydrophobic material.

7 Claims, 8 Drawing Sheets

Fig. 14

REFERENCE ELECTRODE

TECHNICAL FIELD

The present invention relates to a reference electrode for generating reference potential, and, more particularly, to a solid type reference electrode constituted in such a manner that the surface of the conductive substrate thereof is coated with a high molecular film.

BACKGROUND ART

Hitherto, there has been used an electrochemical reference electrode of a type whose electrode potential does not substantially change in a system in which the ion concentration in the fluid to be experimented upon changes, in particular, the hydrogen ion concentration, and the measuring temperature change. A known reference electrode of this type is exemplified by a saturated calomel electrode, a silver/silver chloride electrode and a hydrogen electrode. Furthermore, in recent years, a so-called a hybrid type electrode has been studied in which an organic film made of, for example, polystyrene and polyparaxylylene is formed on a gate insulator film of an MOS (Metal Oxide Semiconductor) type field effect transistor (to be called "an MOSFET" hereinafter).

However, the saturated calomel electrode or the like of the above-described conventional reference electrodes arises a problem in that the size thereof cannot be easily reduced due to the existence of liquid junctions between the reference electrolyte solution and its container.

On the other hand, the MOSFET, in which the gate insulator film thereof is coated with an organic film made of, for example, polystyrene, can be easily miniaturized since it is a solid state device and manufactured by utilizing semiconductor manufacturing technology. However, the MOSFET raises a problem in that its equilibrium potential involves an excessively large drift and raises another problem in that its potential can be easily affected by the ion concentration such as the hydrogen ion.

The silver/silver chloride electrode having an internal fluid chamber in which KCl saturated solution is enclosed usually comprises an electrode in the form of a glass chamber the diameter of which is 2 to 3 cm exhibiting an excellent communication with the external solution. In this case, it is necessary that the internal $K^+$ and $Cl^-$ ions and the external $Cl^-$ ions can easily communicate with one another. Therefore, a problem arises in that the potential can be changed due to the affection of the contamination of internal fluid and the affection of the external $Cl^-$ ions.

In order to overcome the above-described problems, there have been the following desires:

(1) The flowing out of the internal AgCl and KCl must be prevented as much as possible.

(2) An in-phase structure of Ag/AgCl must be constituted.

(3) The reference potential can be displayed without being affected by the $Cl^-$ ions regardless of the fluid to be experimented ($Cl^-$ included).

An object of the present invention is to provide a stable microminiaturized solid (hybrid) reference electrode which is substantially free from outflow of halide.

Another object of the present invention is to provide a reference electrode which can be easily miniaturized, is not affected by ion concentration, provides a stable potential, has excellent stability and high durability.

In order to overcome the above-described problems, the reference electrode according to the present invention is characterized by comprising: a conductive substrate; and insulating and/or hydrophobic material layer formed by neutron or atomic beam sputtering method and covering the surface of the conductive substrate, the insulating and/or hydrophobic material layer containing silver halide dispersed therein.

The reference electrode according to the present invention is characterized by comprising: a conductive substrate; and a laminate film obtained by laminating alternately a thin layer of silver halide and a thin layer of an insulating and/or hydrophobic material, the laminate layer covering the surface of the conductive substrate.

The reference electrode according to the present invention is characterized by comprising: a field effect transistor; and the insulating and/or hydrophobic material layer containing silver halide dispersed therein or the laminate film, formed on the surface of a gate insulator layer of the field effect transistor, or the insulating and/or hydrophobic material layer containing silver halide dispersed therein or the laminate film, formed on the surface of the gate insulator layer of the field effect transistor via a silver thin layer.

The conductive substrate is a substrate formed by silver or a substrate obtained by forming a silver layer on an insulating body. It is preferable that the silver halide be any of silver chloride, silver bromide, and silver iodide. The silver halide may contain an oxidizing agent selected from potassium ferricyanide, potassium chromate, potassium perchlorate or the like or other halide salt mixed thereto. It may be only a mixture of the oxidizing agent selected from potassium ferricyanide, potassium chromate, potassium perchlorate or the like and the halide salt. It is preferable that the insulating and/or hydrophobic material be any of fluorine organic compound (a fluororesin), polytetrafluoroethylene, aromatic polyparaxylylene and polystyrene.

It is preferable that a hydrophilic layer or an ion permeable layer be formed on the surface of the insulating and/or hydrophobic material layer or the laminate film for the purpose of improving antithrombus characteristics, separating impurity ions or the like and transmitting ions, in particular, transmitting chloride ions. It is preferable that the above-described layer comprises a perfluoro-ion exchange layer such as polyvinyl chloride-polyethylene glycol copolymer, styrene-hydroxyethylmethaacrylate (St-HEMA) copolymer, styrene-hydroxyethylmethaacrylate block polymer, polyurethane, polyvinyl alcohol, polyhydroxyethylmethaacrylate, polyacrylamidegel, and polyperfluorosulfonic acid.

According to the present invention, a miniaturized stable solid (hybrid type) reference electrode which is almost free from outflow of silver halide can be provided.

Specifically, (1) Since it is covered with an insulating and/or hydrophobic material layer and the neutral atomic beam method is employed, silver halide cannot easily flow out by virtue of the structure of the material designed in the atomic or molecular state.

(2) Since the electrode according to this mode is, in a state of silver halide and Ag (evaporated), applied to the surface of the ITO glass, $Ag^+$ ions can be always supplied from the substrate. Furthermore, the silver halide is in the form of a land surrounded by tetrafluoroethylene substrate. Therefore, the silver halide/Ag electrode of in-phase structure can be constituted.

(3) The AgCl portion can be easily applied to a miniaturized sensing portion since the above-described method (the neutral or atomic beam sputtering method) is employed. As a result, it can be used as a reference electrode for an ISFET (Ion Selective Field Effect Transistor), and can also be widely used as a hybrid reference electrode for other miniaturized sensors.

When the reference electrode having the above-described laminate film is dipped into water solution, water molecules penetrate a thin layer of the insulating and/or hydrophobic material of the laminate film. Therefore, halide ions of constant concentration generate in the silver halide layer, causing the silver/silver halide in the first layer to generate a certain potential. That is, each of the silver halide layers serves as the reference electrolyte solution and the reference liquid chamber of the conventional reference electrode. Therefore, the above-described reference electrode is dipped into water solution together with the ion electrode so as to use it as an electrode for generating reference potential at the time of measuring ion concentration or the other operations so that the ion concentration is obtained by measuring the difference in the potential between the reference electrode and the ion electrode.

According to the reference electrode according to the present invention, the structure is arranged in such a manner that the laminate film obtained by alternately layering the thin layer of silver halide and a thin layer of an insulating and/or hydrophobic material is applied to the surface of the conductive substrate so that a solid-type reference electrode is formed. Therefore, it can be easily miniaturized, is not affected by pH, chloride ion concentration or the like, provides a constant potential, and has satisfactory stability and high durability.

Furthermore, since the structure is arranged in such a manner that a laminate film obtained by alternately laminating different thin layers is used for the coating, the combination of materials can be easily performed. In addition, since the atomic beam sputtering apparatus can be used for forming the laminate film, the layering can be conducted at room temperature. Furthermore, high dimensional accuracy can be realize at the time of forming a pattern. Therefore, a mass production can be enabled when it is included in a semiconductor manufacturing process. In addition, since the electrode can be operated even if the thickness of the laminate film is less than 1000Å, it can be used as a reference electrode to be used integrally with a sensor for use in a miniaturized range of $\mu$m or less.

The above-described effects can be further effectively improved by arranging the structure in such a manner that the conductive substrate is formed by silver, the substrate arranged such that silver layer is formed on the surface of the insulating material, the silver halide is selected from any of silver chloride, silver bromide, and silver iodide and the insulating and/or hydrophobic material is selected from polytetrafluoroethylene, aromatic polyparaxylyene and polystyrene.

Other and further objects, features and advantages of the invention will be appear more fully from the following description.

BEST MODE FOR CARRYING OUT THE INVENTION

First, neutral atomic beam sputtering employed in the present invention will be described. The neutral atomic beam sputtering is a method of introducing inert gas such as argon so as to be ionized by ionizing plasma, accelerating the ions in a strong electric field, and neutralizing the charge by electrons so that argon atomic beams are generated. The target atoms or molecules are emitted by kinetic energy of the argon atomic beams so as to be accumulated onto the desired substrate. The above-described method is characterized by using a principle of directly converting the kinetic energy of argon into kinetic energy of the target atoms or molecules. Therefore, it is not affected by electrification or a charge and the target can be layered without being heated excessively. In particular, since the target can be layered without any damage or change in its film composition due and without thermal deformation of the film composition, the neutral atomic beam sputtering can be suitably employed when an organic film is layered.

Figure 2A:
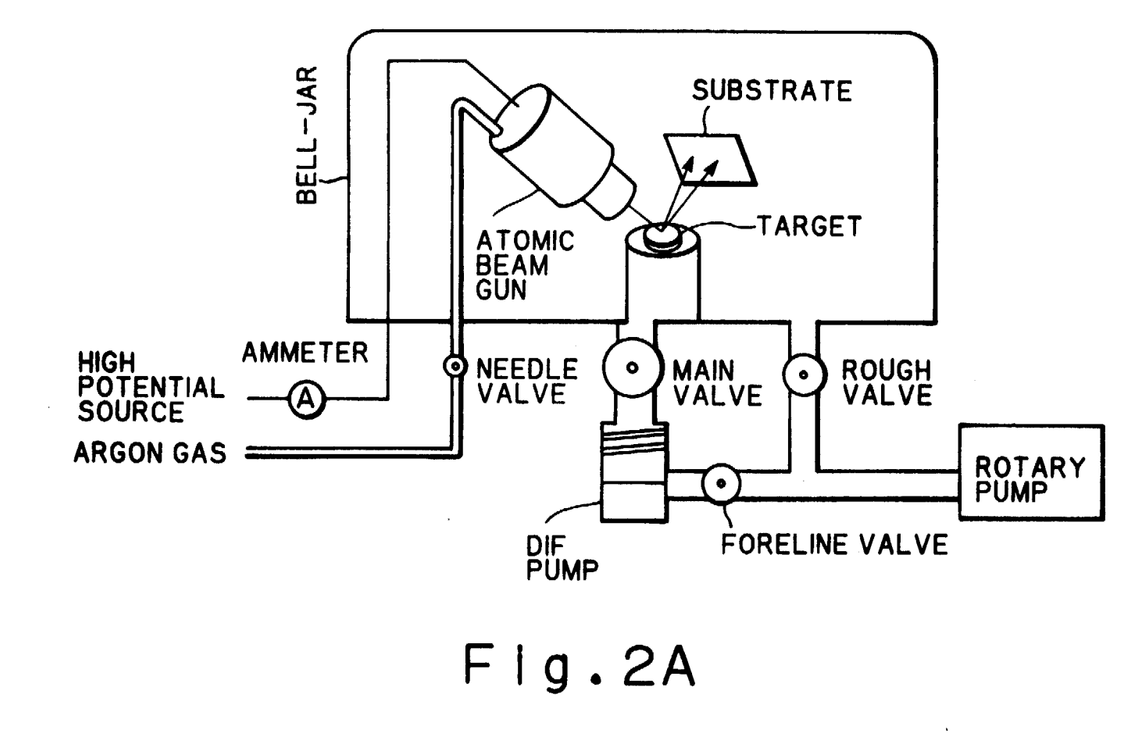
FIG. 2A is a schematic view which illustrates an apparatus for performing atomic beam sputtering and an atomic beam gun used in the present invention.

The apparatus and an atomic beam gun for use in the neutral atomic beam sputtering method are shown in FIG. 2A. Experimental conditions in this case were as follows:
Output: 10 W (5 KV, 2 mA)
Degree of vacuum: $3 \times 10^{-5}$ Torr or less
Time: optional
Atomic beam: argon An insulating and/or hydrophobic material layer including dispersed silver chloride to be layered is arranged to be 500Å to 100 μm in thickness, preferably 500 to 1000Å in thickness.

Examples of the insulating and/or hydrophobic material included tetrafluoroethylene (Teflon ®: manufactured by Dupont), polystyrene, fluorine organic compounds and aromatic polyparaxylylene. The phrase "an insulating material" hereinafter refers to an insulating material and/or a hydrophobic material.

<Mode 1>

Figure 1:
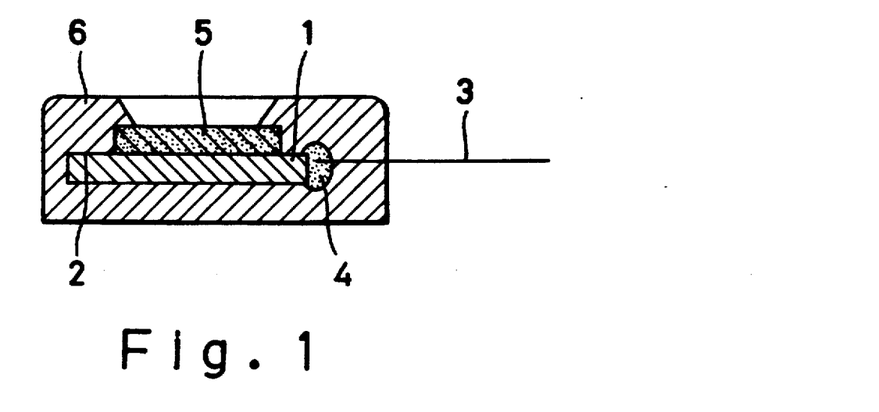
FIG. 1 is a schematic view which illustrates the structure of a reference electrode according to the present invention.

The reference electrode according to this mode is shown in FIG. 1.

Figure 2B:
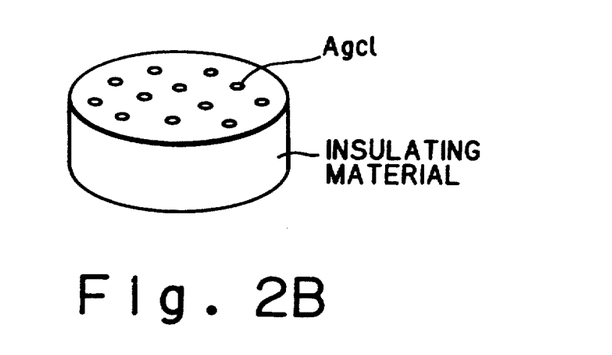
FIG. 2B illustrates an example of a target employed in the present invention.

In an argon atomic beam sputtering apparatus shown in FIG. 2A, an about 2000Å thick silver layer 2 was formed by evaporating on a side of indium tin oxide glass (ITO) 1 so that a substrate was manufactured. A target shown in FIG. 2B (a target manufactured by embedding silver chloride in a Teflon ® disc manufactured by Dupont) was used so as to manufacture an about 1000Å thick insulating material layer 5 in which silver chloride was dispersed in tetrafluoroethylene. Thus, an electrode whose basic layer comprised the silver layer 2 and coated with silver/silver chloride mixture layer was manufactured. During manufacturing the insulating material layer 5, the electrode was protected by a resist and copper wire 3 serving as a lead wire was connected by phosphor bronze 4 (a contact). After the electrode had been sufficiently surrounded by an epoxy resin 6 serving as an insulating material, the resist was separated by acetone.

The manufacturing conditions were as follows:
Output: 10 W (5 KV, 2 mA)
Degree of vacuum: $3 \times 10^{-5}$ Torr
Time: 8 hours The thus manufactured electrode was subjected to annealing (120° C., 10 hours) so as to disperse and stabilize the layer.

<EXPERIMENTAL EXAMPLE 1>

The electrode manufactured by the method according to Mode 1 was employed as the working electrode and a saturated calomel electrode was employed to serve as a comparison electrode. The pH density was adjusted by HCl− and KOH, where [Cl−]: constant. The potential of the electrode was measured with the pH density changed from 1 to 10.

Figure 3:
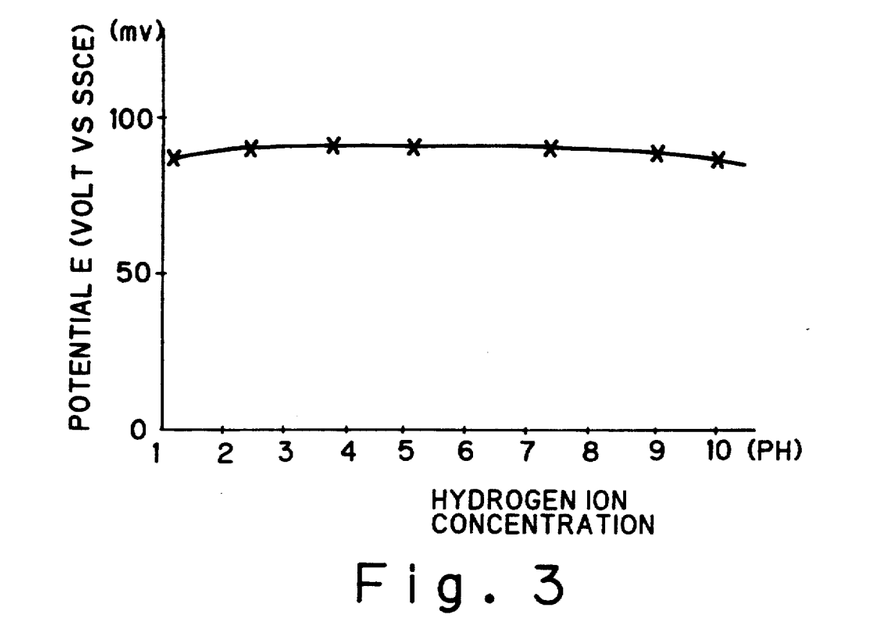
FIG. 3 illustrates potential change with respect to the hydrogen ion concentration in the reference electrode according to the present invention.

The results are shown in FIG. 3. As is shown, since no significant potential change was displayed, the electrode according to this mode can be used as a reference electrode.

<EXPERIMENTAL EXAMPLE 2>

Figure 4:
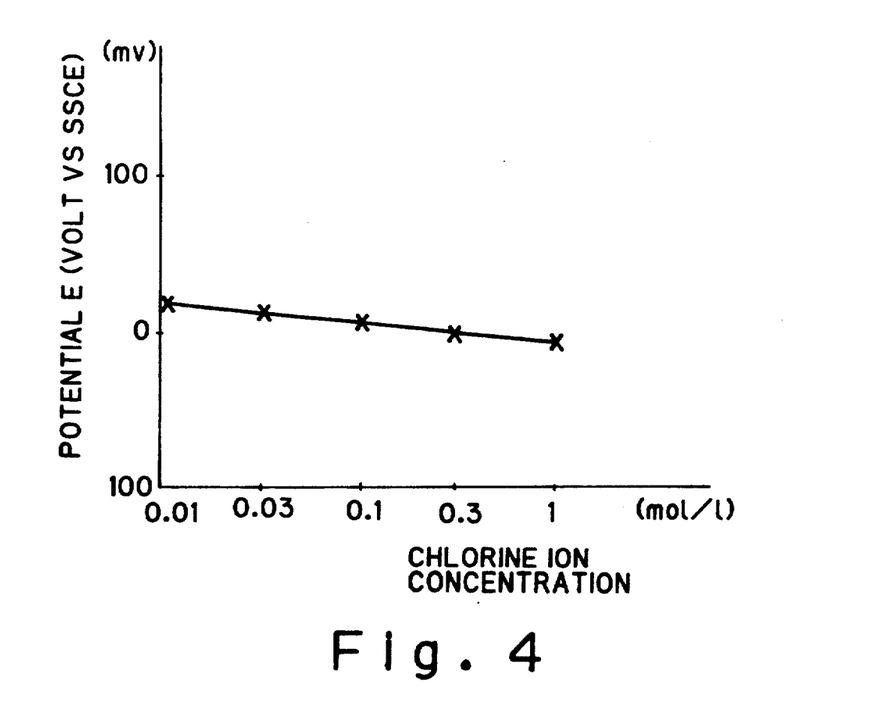
FIG. 4 illustrates potential change with respect to the chlorine ion concentration in the reference electrode according to the present invention.

The electrode manufactured by the method according to Mode 1 was employed as the working electrode and a saturated calomel electrode was employed to serve as a comparison electrode so as to examine the affection of Cl− ion concentration (the KCl concentration was changed from $10^{-2}$ M/l to 1.0 M/l). The obtained results are shown in FIG. 4.

As is shown, the electrode according to this mode is not affected by the Cl− ion concentration. Therefore, it was found that the electrode according to this mode can be used as a reference electrode under the existence of Cl− ions.

As described above, the reference electrode according to this mode exhibits the following advantages:

(1) Since it is covered with an insulating material layer and the atomic beam method is employed, AgCl cannot be easily flowed out by virtue of the tetrafluoroethylene structure designed in the atomic or molecular state.

(2) Furthermore, since the tetrafluoroethylene layer is arranged to be a thin layer of 1000Å or less, preferably 500 to 1000 satisfactory response speed can be obtained. If it exceeds 100 μm, the response speed can be lowered or the separation of the layer takes place.

(3) Since the electrode according to this mode is, in a state of silver halide and Ag (evaporated), applied to the surface of the ITO glass, Ag+ ions can be always supplied from the substrate. Furthermore, the silver halide is in the form of a land surrounded by a polyfluoroethylene substrate. Therefore, the silver halide/Ag electrode of in-phase structure can be constituted.

(4) The AgCl portion can be easily applied to a miniaturized sensing portion since the above-described method (the neutral atomic beam sputtering method) is employed.

As a result, it can be used as a reference electrode for an ISFET (Ion Selective Field Effect Transistor), and can also be widely used as a hybrid reference electrode for other miniaturized sensors.

<Mode 2>

Figure 5:
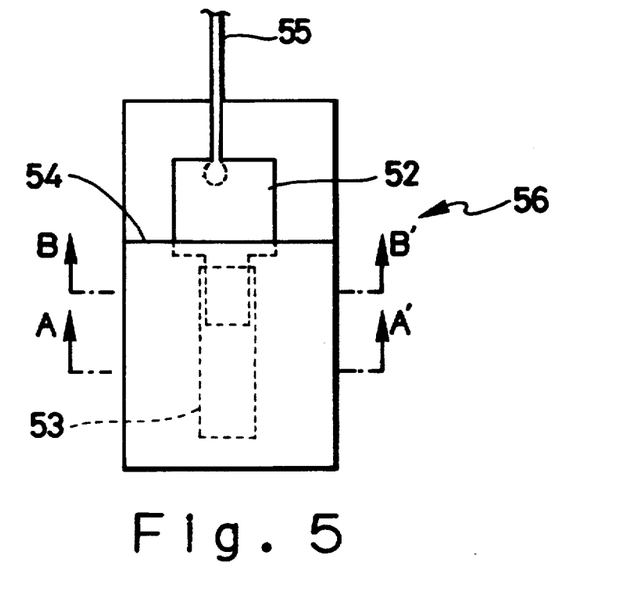
FIG. 5 is a plan view which illustrates Modes 2 to 4 of the reference electrode according to the present invention.
Figure 6:
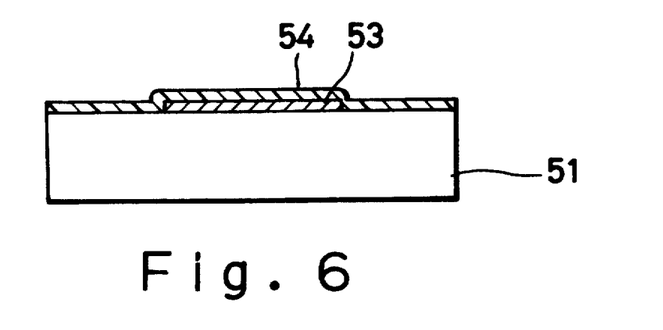
FIG. 6 is a cross sectional view taken along line a—a' in FIG. 5.
Figure 7:
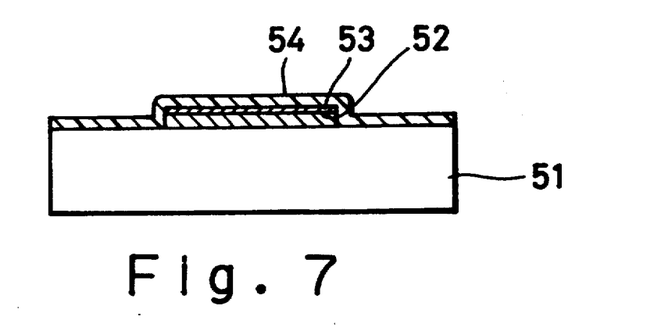
FIG. 7 is a cross sectional view taken along line b—b' in FIG. 5.

FIG. 5 is a plan view which illustrates the reference electrode according to Mode 2 of the present invention. FIG. 6 is a cross sectional view taken along line A—A' in FIG. 5, and FIG. 7 is a cross sectional view taken along line B—B, in FIG. 5.

Figure 8:
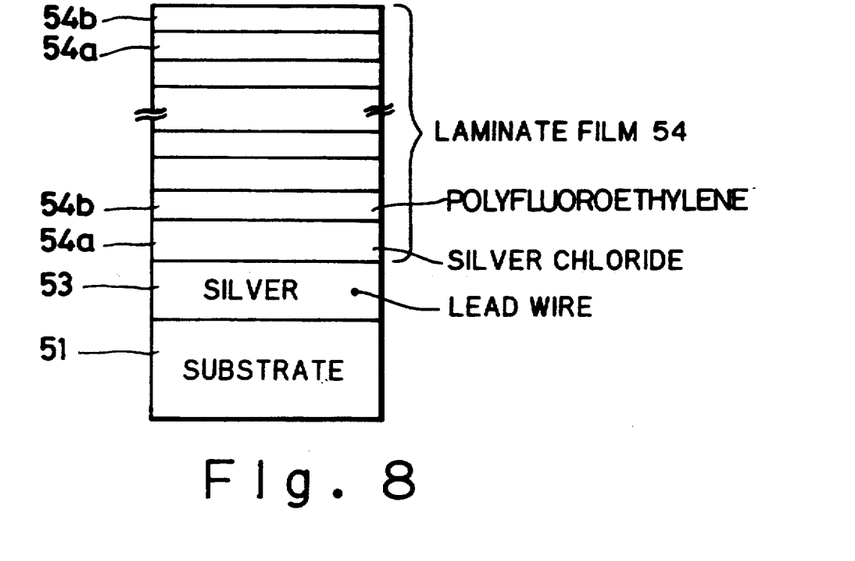
FIG. 8 is a schematic view which illustrates the cross-sectional structure of the Modes 2 to 4 of the reference electrode according to the present invention.

A pattern of chrome thin layer (about 500:52 and a pattern of silver thin layer (about 1000:53 as shown in FIG. 5 were successively formed by a lift-off method on the reverse side of a sapphire substrate (plane azimuth (1102), 15 mm × 15 mm × 0.4 mm) 51 by using a CD sputtering apparatus (manufactured by Aneruba) so that an electrode substrate was manufactured. Similarly, the electrode pattern shown in FIG. 5 was formed on the surface of a isotropic alumina substrate and a grazed alumina substrate. Then, argon atomic beams (high speed atomic beams formed by ionizing and accelerating argon gas at 7 Kv and again neutralizing it by supplying an electron shower) of a current value of 1.15 to 1.2 mA were alternately applied to a silver chloride target and a target made of polytetrafluoroethylene resin (trade mark: Teflon ®) for each 30 minutes for 6 hours so as to accumulate particles emitted therefrom on the surface of the electrode substrate. As is shown from the schematic cross sectional structure shown in FIG. 8, an about 300 to 500Å thick laminated film 54 was formed. The thickness of each of a silver chloride layer 54a and a polytetrafluoroethylene resin layer 54b of the laminated film 54 was 30 to 50Å. Then, a lead wire 55 was, by using a conductive adhesive (C-850-6, manufactured by Amicon), connected to a chrome thin layer 52 of the electrode substrate on which the above-described laminated film 54 had been formed. Then, in order to prevent the appearance of the connection portions of the lead wire 55, the chrome thin layer 52 and the silver thin layer 53, silicone resin (PR×305 clear, manufactured by Toray Silicone) was applied and dried. As a result, a reference electrode 56 was manufactured.

<EXPERIMENTAL EXAMPLE 3>

Figure 10:
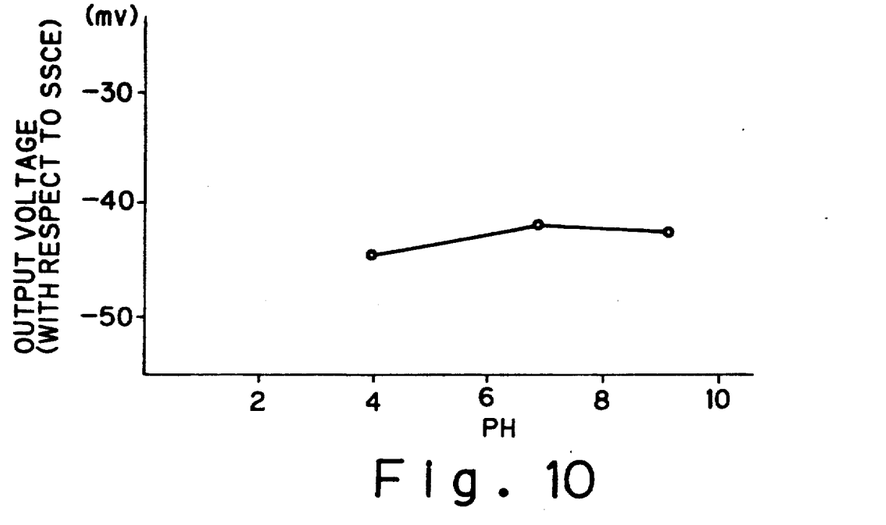
FIG. 10 is a characteristic drawing which illustrates the pH dependency of the potential of the reference electrode according to Mode 2.

The reference electrode 56 thus manufactured was dipped into saturated sodium chloride solution, and then it was taken out after 0, 25, 45, 161 and 288 hours had passed. Then, it was dipped, together with saturated sodium chloride calomel electrode (to be abbreviated to "SSCE" hereinafter) 58 on the market, into standard buffers (manufactured by Wako) 57 of pH 4.01, 6.86 and 9.18. Then, the output potential (Vout) from the electrode 56 with respect to an SCE 59 was measured with phosphate buffer 57 stirred by a stirrer 58. Change in the output potential from the electrode with respect to the pH value of the solution is shown in FIG. 10. As is shown from FIG. 10, it has been found that the reference electrode according to this mode displays substantially constant potential regardless of the pH value. However, the durability of each of the electrodes except for the electrode having the sapphire substrate was unsatisfactory, that is, the life was about 40 days.

<EXPERIMENTAL EXAMPLE 4>

Figure 11:
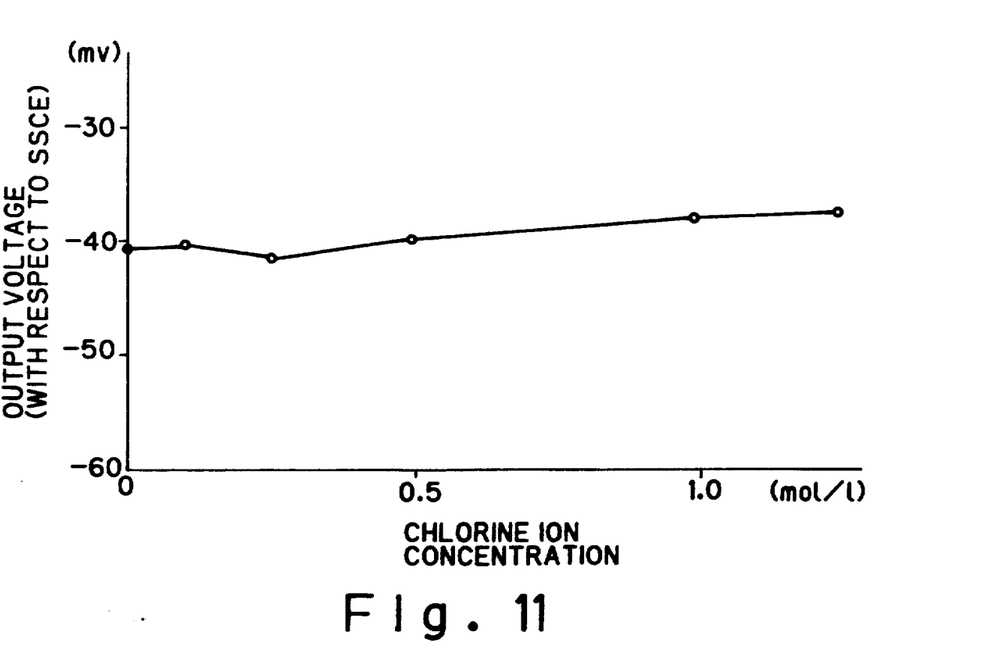
FIG. 11 is a characteristic drawing which illustrates the chlorine ion concentration dependency of the potential of the reference electrode according to Mode 2.

The reference electrode 56 having the sapphire substrate manufactured by the method according to Mode 2 was dipped into saturated sodium chloride solution for 45 hours after it had been manufactured. During the above-described preservation period, the dependency of the potential upon the chloride ion concentration was evaluated. Although the measuring method was arranged to conform to Experimental Example 3, a standard buffer of pH 6.86 was used as the test liquid and the chloride ion concentration was changed by dissolving sodium chloride into the above-described standard buffer so that the output potential from the electrode 56 with respect to SSCE 59 was measured. Change in the output potential from the electrode 56 with respect to the chloride ion concentration in the solution is shown in FIG. 11. As a result, it has been confirmed that the reference electrode 56 according to this mode displays substantially constant potential regardless of the chloride ion concentration. Furthermore, the characteristics of the electrode 56 were examined after it has been preserved in the above-described solution for 100 days. The reference electrode 56 was not affected by the pH value if it was in the range between pH 4 and pH 9.2. Furthermore, it has been confirmed that the potential did not change in the range of the chloride ion concentration between 0 and 1 M.

<Mode 3>

Figure 12:
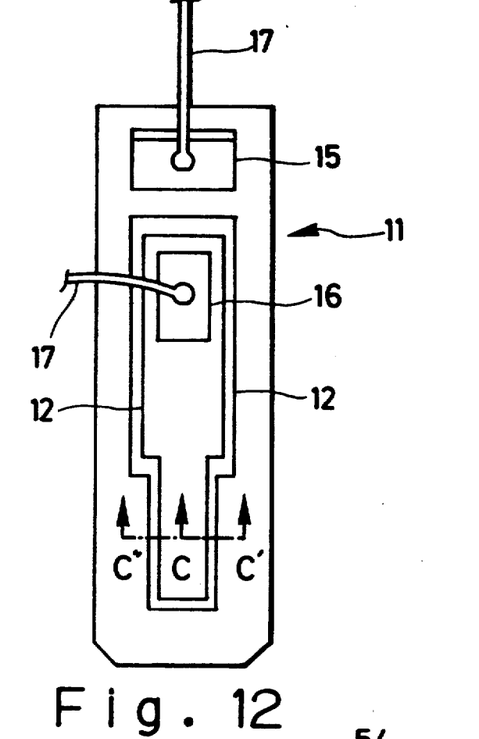
FIG. 12 is a plan view which illustrates the structure of Modes 3 and 4 of the reference electrode according to the present invention.
Figure 13:
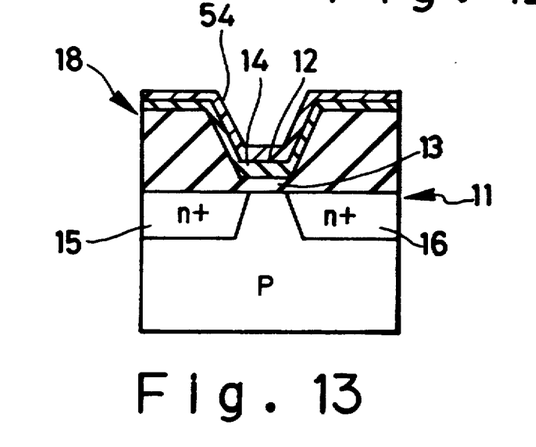
FIG. 13 is a cross sectional view taken along line C—C' in FIG. 12 which illustrates Mode 3.

As shown in FIGS. 12 and 13, the laminated film 54 formed by silver chloride and polytetrafluoroethylene resin was formed on the surface of the gate insulator layer 12 of the MOS-type ISFET (Ion Selective Field Effect Transistor) 11 in accordance with the method employed in Mode 2. Ten layers each of which was about 700Å in thickness were laminated. As the gate insulator layer 12, a pH-ISFET electrode having an insulator layer structure of oxide silicon layer (1000Å) 13/nitride layer (1500Å) 14 was employed, where a lead wire 17 had been previously adhered to a source region 15 and a drain region 16. FIG. 13 illustrates the cross-sectional structure taken along line C—C' of a reference electrode 18 manufactured according to this mode shown in FIG. 12.

<EXPERIMENTAL EXAMPLE 5>

Figure 9A:
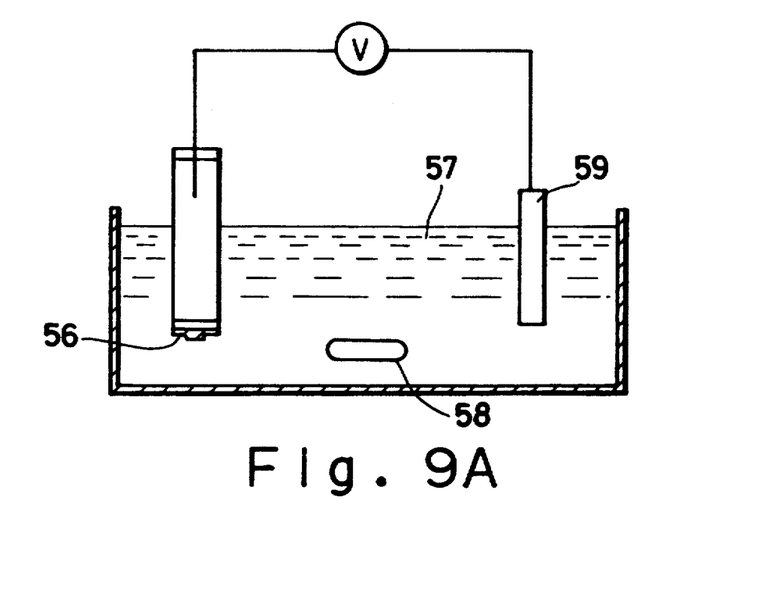
FIGS. 9A and 9B are schematic structural views each of which illustrates an apparatus for measuring the characteristics of Modes 2 to 4 of the reference electrode according to the present invention.
Figure 9B:
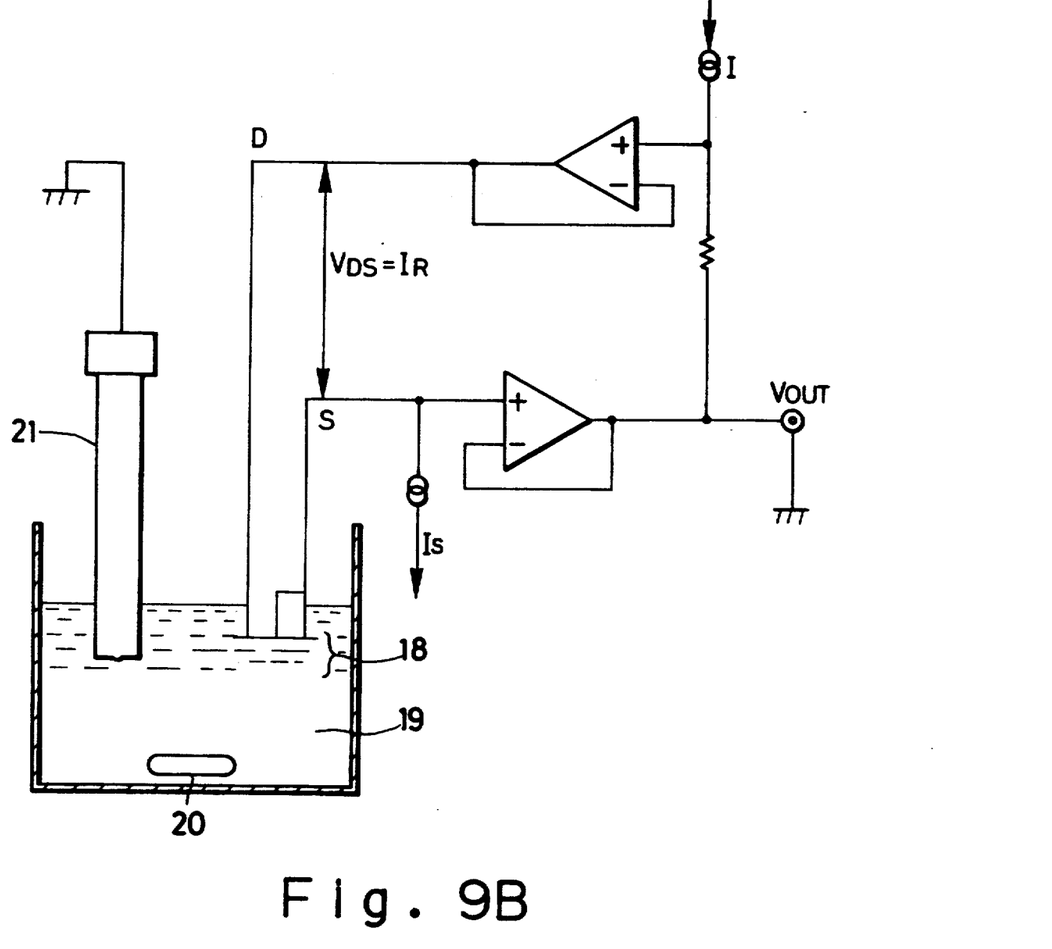

The reference electrode 18 according to Mode 3 was dipped into phosphoric acid buffer 19 in a measuring apparatus shown in FIG. 9B. The output potential (Vout) of the electrode 18 with respect to SSCE 21 was measured with the phosphoric acid buffer 19 stirred by a stirrer 20 so that the ph dependency and the chloride ion concentration dependency were examined. As a result, constant potential within an experimental error (±1 mV) was generated in the range between pH 1 and pH 10. Therefore, it was confirmed that the electrode 18 has substantially no pH value dependency and the chloride ion concentration dependency The measuring conditions were arranged in this case that $V_{DS}=4$ V and $I_S=50$ μA. The gate potential was shifted in the negative direction by 1.0 to 1.5 V with respect to a pH electrode having no laminated layer 4. However, the electrode 18 can be employed as the satisfactory reference electrode for a semiconductor sensor if its output voltage is shifted.

<Mode 4>

Figure 14:
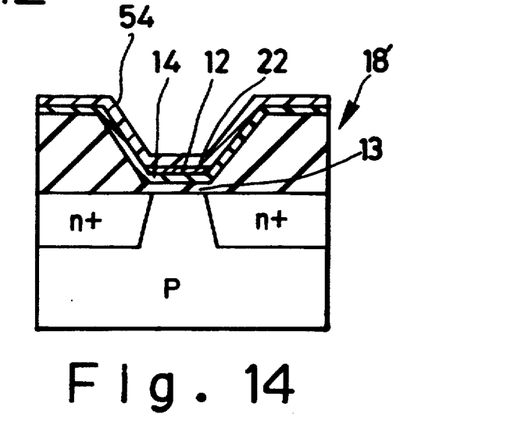
FIG. 14 is a cross sectional view taken along line C—C" in FIG. 12 which illustrates Mode 3.

Similarly to Mode 3, a silver thin layer (thickness: 50 to 300Å) 22 was vacuum-evaporated onto the surface of the ISFET gate insulator layer 12 as shown in FIG. 14 Then, the laminated film (thickness: 700Å) 54 of silver chloride and polytetrafluoroethylene resin was laminated on the entire surface of the silver thin layer 22 by the method which is the same as that employed in Mode 2. FIG. 14 illustrates the cross-sectional structure taken along line C—C' of a reference electrode 18' manufactured according to this mode shown in FIG. 14.

EXPERIMENTAL EXAMPLE 6>

The above-described reference electrode was subjected to an evaluation about the pH dependency and the chloride ion concentration dependency similarly to Mode 5. The electrode was not affected by the above-described factors in the range between pH 1 and pH 10 and in the range between the chloride ion concentration of 0 and 1M. Furthermore, no excessive negative shift of the gate potential, which had been taken place in Mode 3, was not observed.

Although a preferred form of the invention has been described with a certain degree of particularly, it is understood that the present disclosure of the preferred form has been changed with respect to details of construction and the combination and arrangement of parts without departing from the spirit and the scope of the invention as hereinafter claimed.

What is claimed is:

1. A reference electrode comprising:
   a conductive substrate; and
   a laminate film including a laminate layer of several alternate layers of silver halide and an insulating and hydrophobic material selected from fluorine organic compound (fluororesin), polytetrafluoroethylene, aromatic polyparaxylene and polystyrene, said laminate layer covering the surface of said conductive substrate and having said layer of insulating and hydrophobic material at an outer most surface.

2. A reference electrode comprising:
   a field effect transistor; and a laminate film including a laminate layer of several alternate layers of silver halide and an insulating and hydrophobic material selected from fluorine organic compound (fluororesin), polytetrafluroethylene, aromatic polyparaxylene and polystyrene, said laminate layer covering the surface of said conductive substrate and having said layer of insulating and hydrophobic material at an outer most surface, said laminate film covering a surface of a gate insulator layer of said field effect transistor.

3. A reference electrode comprising:
a field effect transistor; and
a laminate film including a laminate layer of several alternate layers of silver halide and an insulating and hydrophobic material selected from fluorine organic compound (fluororesin), polytetrafluroethylene, aromatic polyparaxylene and polystyrene, said laminate layer covering the surface of said conductive substrate and having said layer of insulating and hydrophobic material at an outer most surface, said laminate film covering a surface of a gate insulator layer of said field effect transistor via a silver thin layer.

4. A reference electrode according to claim 1, wherein said silver halide is selected from silver chloride, silver bromide, silver iodide and silver fluoride.

5. A reference electrode according to claim 1, wherein said silver halide contains an oxidizing agent selected from potassium ferricyanide, potassium chromate and potassium perchlorate or other halide salt mixed thereto.

6. A reference electrode according to claim 1, wherein said conductive substrate comprises a substrate formed by silver or a substrate obtained by forming a silver layer on an insulating body.

7. A reference electrode according to claim 1, a hydrophobic layer or an ion permeable layer is further formed on a surface of said laminate film.

* * * * *

UNITED STATES PATENT AND TRADEMARK OFFICE
CERTIFICATE OF CORRECTION

PATENT NO. : 5,200,053

DATED : April 6, 1993

INVENTOR(S) : Takeshi SHIMOMURA et al

It is certified that error appears in the above-identified patent and that said Letters Patent is hereby corrected as shown below:

On the title page,
  Item: [87], delete "Jan. 6, 1989" and insert -- June 1, 1989 --.

In Column 6, line 39, delete "B," and insert -- B' --.

In Column 8, line 49, delete "particularly" and insert -- particularity --.

In Column 8, line 51, delete "has been" and insert -- may be --.

Signed and Sealed this

Eighth Day of February, 1994

Attest:

BRUCE LEHMAN

*Attesting Officer*    *Commissioner of Patents and Trademarks*